(12) United States Patent
Morales et al.

(10) Patent No.: US 10,405,980 B2
(45) Date of Patent: Sep. 10, 2019

(54) STABILIZER FOR OPERATIONS ON THE BEATING HEART

(71) Applicant: AESCULAP AG, Tuttlingen (DE)

(72) Inventors: Pedro Morales, Tuttlingen (DE); Stefanie Schabert, Aldingen (DE); Jochen Cremer, Heikendorf (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/439,015

(22) PCT Filed: Oct. 24, 2013

(86) PCT No.: PCT/EP2013/072244
§ 371 (c)(1),
(2) Date: Apr. 28, 2015

(87) PCT Pub. No.: WO2014/067841
PCT Pub. Date: May 8, 2014

(65) Prior Publication Data
US 2015/0297347 A1 Oct. 22, 2015

(30) Foreign Application Priority Data
Oct. 29, 2012 (DE) .................. 10 2012 219 752

(51) Int. Cl.
*A61F 2/24* (2006.01)
*A61B 17/02* (2006.01)

(52) U.S. Cl.
CPC ............ *A61F 2/2481* (2013.01); *A61B 17/02* (2013.01); *A61B 2017/0243* (2013.01); *A61B 2217/005* (2013.01)

(58) Field of Classification Search
CPC ............... A61F 2/2481; A61B 17/0206; A61B 2017/005; A61B 2017/0243
See application file for complete search history.

(56) References Cited

U.S. PATENT DOCUMENTS 6,152,874 A 11/2000 Looney et al.
6,478,029 B1 * 11/2002 Boyd ............... A61B 17/00234
128/898

(Continued)

FOREIGN PATENT DOCUMENTS

DE 200 20 598 U1 2/2001
WO 98/27869 A1 7/1998

OTHER PUBLICATIONS

International Search Report PCT/EP2013/072244 dated Jan. 22, 2014.

*Primary Examiner* — Carrie R Dorna
(74) *Attorney, Agent, or Firm* — RatnerPrestia

(57) ABSTRACT

A stabilizer for operations on a heart includes a fastening shaft and a tissue contact component with two elongated bearing elements provided on a base section and adapted to be arranged on two opposing sides of a blood vessel such that at least one section of the blood vessel runs between the two bearing elements, wherein the base section is affixed to one end of the fastening shaft. At least one bearing element has a slit extending longitudinally at least over a section thereof. The fastening shaft has an axially proceeding channel which extends at least over a section of the fastening shaft and is connected to at least one connecting channel in the region of the end of the fastening shaft on which the base section is mounted, the connection channel connecting the axially proceeding channel to the surroundings, wherein the axial end of the fastening shaft is closed.

14 Claims, 4 Drawing Sheets

(56) References Cited

U.S. PATENT DOCUMENTS

| | | | |
|---|---|---|---|
| 6,511,416 B1 * | 1/2003 | Green, II | A61B 17/02 600/37 |
| 2002/0099268 A1 | 7/2002 | Paul et al. | |
| 2003/0060685 A1 | 3/2003 | Houser et al. | |
| 2004/0143168 A1 | 7/2004 | Hu et al. | |
| 2004/0171917 A1 | 9/2004 | Paul et al. | |

* cited by examiner

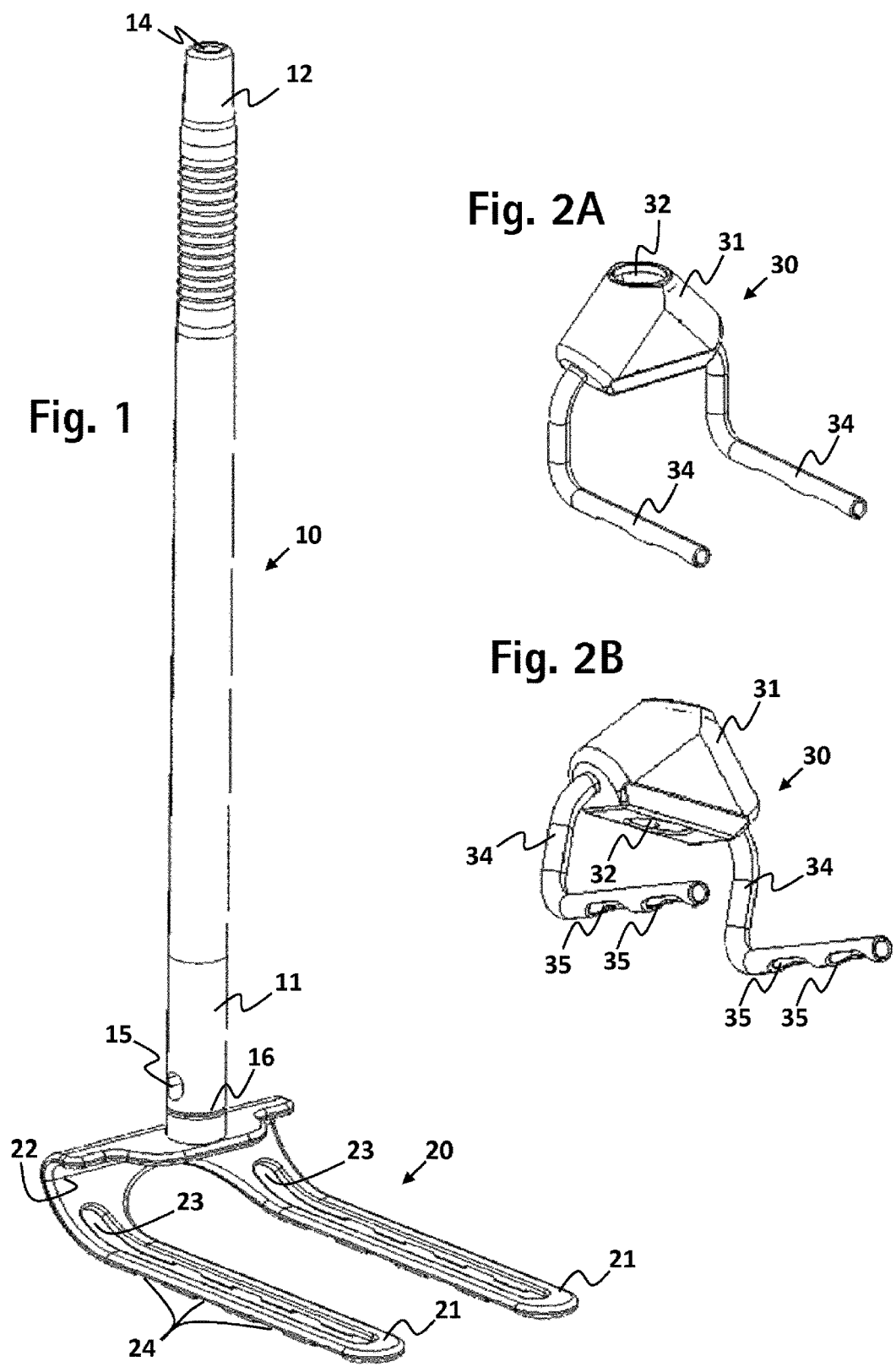

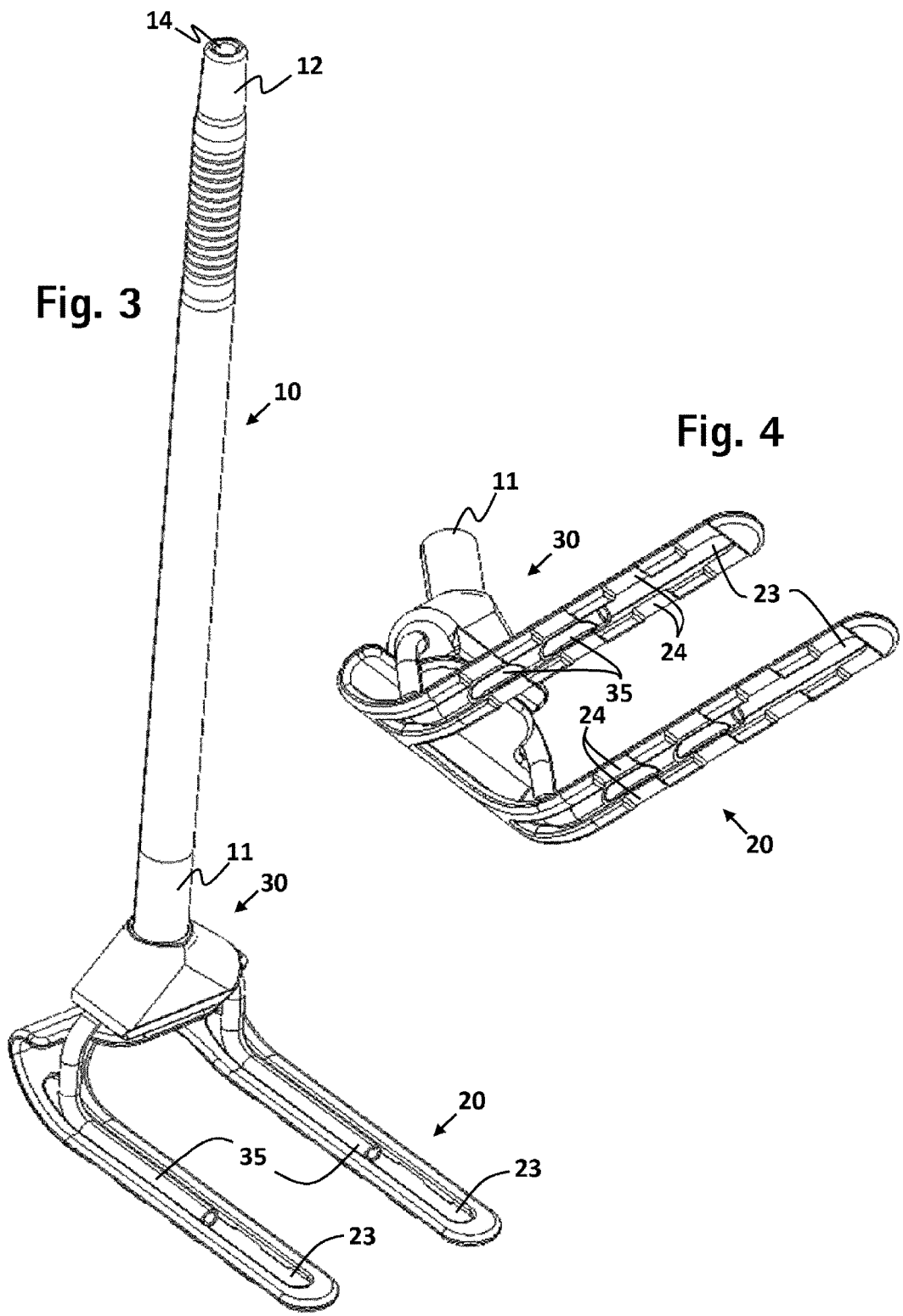

STABILIZER FOR OPERATIONS ON THE BEATING HEART

The present invention relates to a stabilizer for operating on the beating heart, and especially a stabilizer for temporarily and partially calming the heart during an anastomosis on a coronary vessel.

In the state of the art, various devices are known for temporarily stabilizing a region of a heart, especially during anastomosis on a beating heart. For example, a stabilizer is disclosed in the publication US 2004/0143168 A1 in which a tissue contact section is articulated to a fastening shaft. The tissue contact section has two bearing elements which extend parallel to each other from a base section. The free ends of the two bearing elements and the ends with which they are attached to the base section are curved upward like a ski tip in order to prevent damage to the stabilized tissue, especially in the end region of the bearing elements.

A stabilizer is also disclosed in the publication US 2002/0099268 A1 that has two ski-like bearing elements which are provided on a common base section that is mounted on the fastening shaft. In this case, the fastening shaft is replaced by a movable and deformable arm. The tissue contact component is also articulated to the arm here.

SUMMARY OF THE INVENTION AND DETAILED DESCRIPTION

The stabilization function and thus the holding function of the surface of the heart, where the anastomosis or another operation shall take place, is achieved in that the tissue contact component and in particular the bearing sections is pressed against the surface of the heart. In this manner, the operating area is pressed into the heart and is then located on the floor of a trough-shaped recess in the surface of the heart. Since blood exits the open vessels in an anastomosis and in most other operations on the heart as well, this blood collects in the trough-shaped recess that is formed by the respective stabilizer. So that the surgeon has a sufficient view on the operating area, the operation has to be interrupted for a short time, so that the blood can be aspired. In addition to blood, other fluids, especially bodily fluids, can also collect in the operating area. When blood to be aspirated and aspirated blood is mentioned in the following, it always includes other fluids and bodily fluids. It is therefore the aim of the present invention to provide a stabilizer especially for operations on a heart, preferably on a beating heart, in which an interruption of the operation to aspirate collecting blood is unnecessary.

The object of the present invention is achieved by means of a stabilizer according to claim 1. Advantageous embodiments and further developments of the stabilizer according to the invention are the subject matter of the dependent claims.

The stabilizer according to the invention which is suitable for operations on a heart, and especially on a beating heart, has a fastening shaft and a tissue contact component. The tissue contact component possesses two substantially parallel elongated bearing elements which are provided on a base section. In order to minimize the restriction of the surgeon's vision by the fastening shaft, the two bearing elements first extend in a direction away from the base section and are then bent basically 180° in order to extend in the opposite direction. The bearing elements are adapted to be arranged on two opposing sides of a blood vessel so that at least one section of a blood vessel runs between the two bearing elements. Because the bearing elements are pressed into the surface of the heart, lateral stress can be exerted on the operating area between the two bearing elements. Incisions can therefore be made more easily in the operating area in this manner. In addition, the base section of the tissue contact component is attached to one end of the fastening shaft. At least one of the two bearing elements has a slit which extends in the longitudinal direction of the bearing element, at least over a section thereof. Preferably, the cut extends into the vicinity of the free end of the respective bearing element, wherein two parts of the bearing elements are connected to the free ends. More preferably, the structure of the opposite end of the bearing elements is similar. The fastening shaft furthermore also has an axially running channel which extends at least over a section of the fastening shaft and is connected to at least one connecting channel in the region of the end of the fastening shaft to which the base section is affixed. This connecting channel connects the axially proceeding channel to the surrounding area of the fastening shaft. The axial end of the fastening shaft is preferably closed. The at least one connecting channel can be arranged radially in the fastening shaft; it can, however, also be arranged obliquely.

A region of a heart can be stabilized with such a stabilizer. When the openings of the at least one connecting channel are provided in the outer surface of the fastening shaft close to the contact surface of the bearing elements, the blood can be aspirated out of the operating area through these openings by providing a suction device or vacuum to device on the other end of the axial channel in the fastening shaft.

According to one advantageous embodiment of the stabilizer according to the invention, the stabilizer has an aspiration device which is releasably mountable on the fastening shaft. In particular, the aspiration device can be pushed onto the fastening shaft from the direction of its free end. The aspiration device has a connection component with which the aspiration device can be fastened releasably on the stabilizer and which has a least one connection cavity, and has a least one aspiration component which has an axially extending channel that is connected to the at least one connection cavity. The aspiration component is adapted to be arranged at least partially in a slit of a bearing element when the aspiration device is mounted on the stabilizer. If the aspiration device can be pushed or placed on the fastening shaft, the connecting component has a through-hole which corresponds to the outer cross-section of the fastening shaft.

According to another advantageous design of the stabilizer according to the invention, at least one bearing element has at least one groove which extends in the bearing surface of the bearing element substantially transversely to its longitudinal direction. The groove makes it possible for the blood that has collected in the operating area to flow under the bearing element to the aspiration device. In this manner, not only the blood flowing over bearing elements can be aspirated. This improves the result of the aspiration.

According to another advantageous design of the stabilizer according to the invention, the at least one aspiration component of the aspiration device has at least one radial opening which is connected to a groove in the bearing element when the aspiration device is releasably attached to the stabilizer, and the aspiration component is partially arranged in the slit in the bearing element. Such a radial groove is particularly advantageous since the fluid can be aspirated over a longer region in the longitudinal direction of the bearing elements and not just at the axial opening of the aspiration component. If at least one radial opening is provided in the aspiration component, the axial end of the aspiration component can also be closed. Furthermore it is particularly advantageous when the radial openings are connected to the grooves in the bearing surfaces of the bearing elements since blood can also be aspirated directly from the operating area between the two bearing elements of the aspiration component(s). It is particularly advantageous if several radial openings are arranged distributed in the longitudinal direction in the aspiration component, and a plurality of laterally proceeding grooves are correspondingly also formed in the bearing surface of the bearing elements. In addition, an axial opening can also be provided in the aspiration component which prevents the tissue lying on the aspiration component from being aspirated through the radial openings in the aspiration component and thereby perhaps being damaged.

According to one particularly advantageous design of the stabilizer according to the invention, both bearing elements have a lengthwise slit, and the aspiration device has two aspiration components that are connected to the connection component and adapted to be at least partially arranged in the corresponding slit of the bearing element when the aspiration device is affixed to the stabilizer. In this manner, a stabilizer is created with an aspiration device that can aspirate blood on both sides of the operating area.

According to another advantageous design of the stabilizer according to the invention, the aspiration component consists of a curved tube. The free end of the tube preferably does not have any sharp edges, and the outer diameter of the tube is approximately as large as the thickness of the bearing elements. In this matter, an aspiration component is formed that is particularly easy to produce and can be accommodated particularly well in the contacting components and protected by them.

According to another particularly advantageous design of the stabilizer according to the invention, the contact surface of the bearing elements is designed in the longitudinal direction and/or in the transverse direction of the bearing elements such that the edges of the contact surface are rounded or curved up like a ski tip. This can prevent particularly high pressure from being exerted on the surface of the heart in the edge region of the bearing elements which could lead to necrosis. Sharp edges could also cause injurious cuts in the heart. With the above-described structure of the bearing elements or their bottom side, damage to the heart tissue is prevented to the greatest extent possible. The expression "curved like a ski tip" does not necessarily mean that the component must be bent after its manufacture; the respective component can also be formed with a curve. Instead, the expression "curved like a ski tip" refers to a lateral view of a ski in which the tip of the ski is discerned which gently rises from the base, wherein no kink or edge is formed between the ski tip and contact surface of the ski.

According to one particularly advantageous design of the stabilizer according to the invention, the free end of the fastening shaft possesses a connector to which a vacuum device can be affixed, wherein the connector is preferably a luer connector. The blood is hence aspirated through the fastening shaft when slight pressure that predominates in the region of the connection opening and/or the aspiration device is applied to the free end of the fastening shaft.

According to another particularly advantageous design of the stabilizer according to the invention, the fastening shaft has at least one peripheral groove in the region of the end at which the base section is attached, and which is arranged in the vicinity of the at least one connection channel and is adapted to accommodate a seal element. Preferably, the connection component has two peripheral grooves that are formed in its axial passage such that one of these peripheral grooves opposes a peripheral groove in the fastening shaft when the aspiration device is affixed to the stabilizer, wherein the two grooves are adapted to accommodate a sealing component, preferably an O-ring. The grooves in the fastening shaft or connection component are adapted such that the sealing components remain therein when the connection between the fastening shaft and aspiration device is released. The connection component furthermore preferably has an additional peripheral groove between the two other peripheral grooves that at least partially form the connection cavity. In this manner, a stabilizer can be created in which the sealing components, preferably O-rings between the fasting shaft and aspiration device, simultaneously serve as a positioning aid and fastening means. In addition, a connection cavity is created that may possibly connect both aspiration tubes and both connection channels with each other, and is hence less subject to clogging. Two peripheral grooves can also be provided in the fastening shaft on both sides of the connection channel.

Further advantages and characteristics of the invention are apparent to the person skilled in the art from the attached figures and the detailed description of the exemplary embodiments.

FIG. 1 shows an isometric view of a stabilizer according to a first exemplary embodiment;

FIG. 2A shows an isometric view of an aspiration device for the stabilizer of FIG. 1;

FIG. 2B shows a further isometric view of an aspiration device for the stabilizer of FIG. 1;

FIG. 3 shows an isometric view of a stabilizer with an aspiration device according to the first exemplary embodiment;

FIG. 4 shows a section of a stabilizer with an aspiration device according to FIG. 3 from below;

Figure 5:
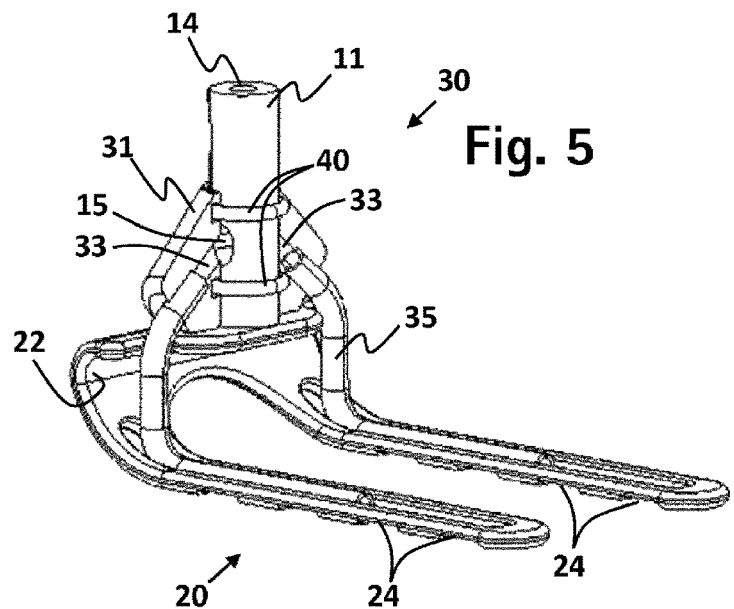
FIG. 5 shows a section of a stabilizer with an aspiration device according to FIG. 3 with a partially cut-away aspiration device.

A first exemplary embodiment of the present invention is described in detail below with reference to FIGS. 1 to 6B.

FIG. 1 reveals a stabilizer for operations on a heart with a fastening shaft 10 and a tissue contact component 20 with two substantially parallel, elongated bearing elements 21, 21 which are provided on a base section 22 and are adapted to be arranged on two opposing sides of a blood vessel B such that at least one section of the blood vessel B runs between the two bearing elements 21, 21, wherein the base section 22 of the tissue contact component 20 is affixed to one end 11 of the fastening shaft 10. Both bearing elements 21, 21 have a slit 23 that extends in the longitudinal direction of the bearing element 21, at least basically over its entire length. The fastening shaft 10 has an axial hole 14 that extends over the entire length of the fastening shaft 10, and its end 11 is closed at which the base section 22 of the tissue contact component 20 is affixed. The axial hole 14 in the fastening shaft 10 is connected to a connection channel 15 that traverses the axial channel 14. In this manner, the connection channel 15 in the fastening shaft 10 forms two openings in the vicinity of the end 11 of the fastening shaft 10.

An aspiration device 30 in this exemplary embodiment consists of a connection component 31 with the assistance of which the aspiration device 30 is releasably attachable by means of two O-rings 40 and corresponding seating grooves 16 (only one seating groove 16 is shown in the figure) to the fastening shaft 10 of the stabilizer in that the through-hole 32 of the connection component 31 is pushed onto the fastening shaft 10 and then toward its end 11 until the O-rings 40 are accommodated in the seating grooves 16, and the floor surface of the connection component 31 lies against the fastening section 22 of the tissue contact component 20. The connection component 31 also has a connection cavity 33.

The aspiration device 30 possesses two suction components 34 that are formed from curved tube elements. The aspiration components 34 have an axial passage which is open to the distal or free end of the tube element. The proximal end of each tube element 34 is connected to the connection component 31 so that the axial passage in each tube element 34 is connected to the connection cavity 33. Furthermore, each tube element 34 has two radial openings 35 that extend to the bottom side of each tube element 34. The tube elements 34 are adapted to be partially arranged in the slit 23 of a bearing element 21 when the aspiration device 30 is mounted on the stabilizer. The outer diameter of the tube elements 34 substantially corresponds to the width of the slit 23 in the bearing element 21. The tube elements 34 furthermore do not extend over the entire length of the slit 23 but rather only over slightly more than one-half of the length of these slits 23.

The bearing elements 21 each have two grooves 24 that extend in the contact surface of the bearing element 21 transversely to the longitudinal direction thereof. The shape and size of the grooves 24 substantially correspond to the radial openings 35 in the tube elements 34 and are arranged such that the radial openings 35 and the grooves 24, at least in several areas of the bearing element 21, lie in a line so that blood and other fluids can flow along the bottom side of the bearing element 21 through a groove 24 toward the radial opening 35.

Figure 6A:
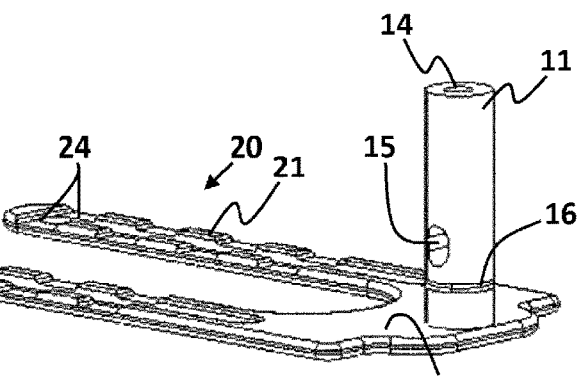
FIG. 6A shows an isometric view of a stabilizer without an aspiration device according to the first exemplary embodiment in a state of being produced.
Figure 6B:
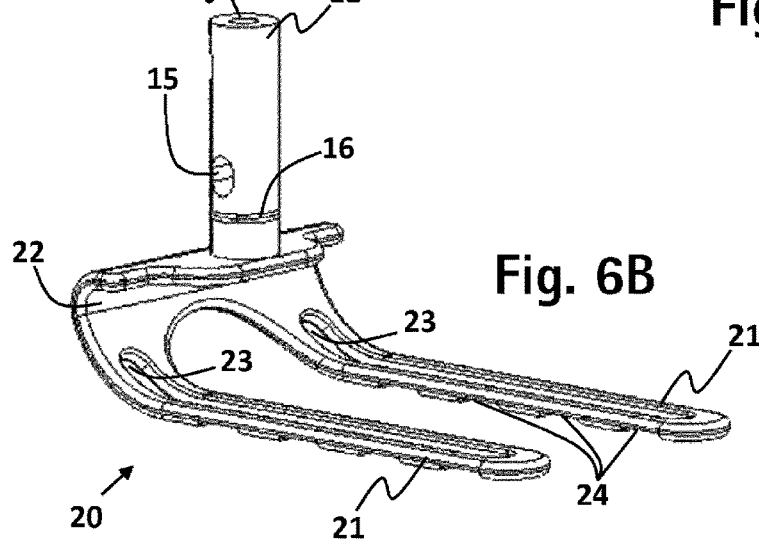
FIG. 6B shows an isometric view of a stabilizer without an aspiration device according to the first exemplary embodiment in a state of being used.

In the present exemplary embodiment, the bearing elements 21 are only curved upward in the shape of a ski in one direction, that is, at the end at which they are connected to the base section 22 as can be seen in particular in FIG. 6B. The free ends of the bearing elements 41 are not curved up, and there is also no upward curve perpendicular to the bearing elements 21. However, the edges of the bearing elements 21 are rounded so that the tissue is not damaged by the sharp edges.

The free end 12 of the fastening shaft 10 is provided with a connector, that is, a luer connector. An aspiration pump can be affixed to this connector, wherein this aspiration pump is preferably specially adapted for surgical purposes. The aspiration pump can be continuously or intermittently in operation.

As described above, the connection component 31 is releasably mounted on the fastening shaft 10 or its end 11 with the aid of two O-rings 40. The O-rings 40 are accommodated in two peripheral inner grooves in the connection component 31. Because the peripheral inner grooves are formed more deeply in the connection component 31 than the peripheral outer grooves in the fastening shaft 10, the O-rings 40 remain at least in the peripheral inner grooves in the connection component 31 and disengage from the grooves 16 in the fastening shaft.

As can be seen in FIG. 5, the fastening shaft 11, the connection component 31, the tube elements 34 and the O-rings 40 form a common cavity through which blood, etc. can be aspirated. So that two cavities are not formed which are exclusively connected by the connection channel 15, another peripheral groove is provided in the connection component 31 that connects the cavities.

If a vacuum source such as a surgical aspiration pump is connected with a hose to the luer connector, blood, etc. can be aspirated out of the trough region W without having to interrupt the operation and restrict the field of view of the operating area. Because the fastening shaft is formed with an inner channel, a hose line to the tissue contact component is not required.

It can be seen in FIGS. 6A and 6B how the tissue contact section 20 is generated in this exemplary embodiment. The base section 22 and the two bearing elements 21 are first formed as a flat component. The bearing elements 21 are then bent in order to generate a ski-shaped upward curve on at least one side. Such a ski-shaped upward curve is especially advantageous because the stress on the tissue underneath in the upwardly curved edge area of the bearing elements 21 is reduced.

Figure 7A:
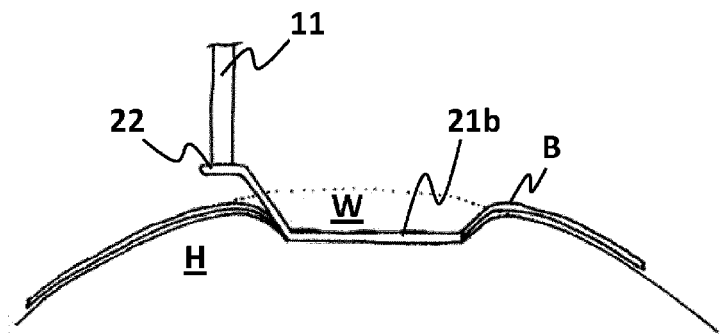
FIG. 7A shows a schematic side view of a stabilizer without an aspiration device according to a second exemplary embodiment.
Figure 8A:
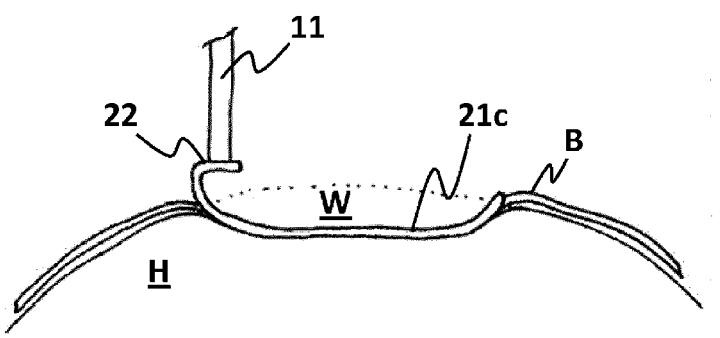
FIG. 8A shows a schematic side view of a stabilizer without an aspiration device according to a third exemplary embodiment.
Figure 7B:
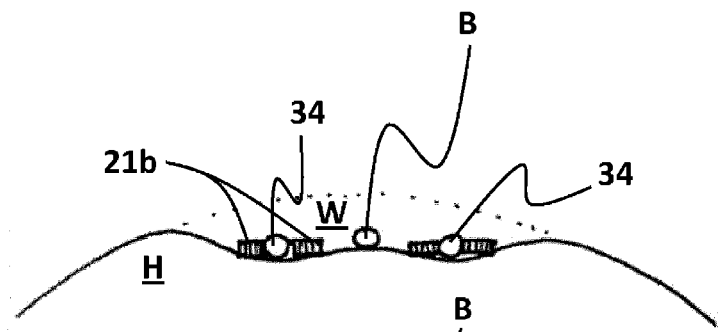
FIG. 7B shows a schematic view of a stabilizer without an aspiration device according to the second exemplary embodiment in the direction of the bearing elements.
Figure 8B:
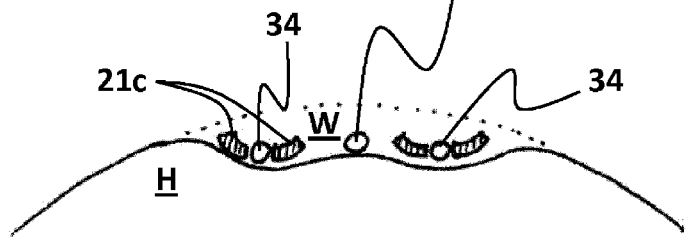
FIG. 8B shows a schematic view of a stabilizer without an aspiration device according to the third exemplary embodiment in the direction of the bearing elements.

FIGS. 7 and 8 show how a stabilizer according to the invention is placed on the surface of the heart H. In order to reliably position the stabilizer relative to the blood vessel B and achieve stabilization of the heart H, the stabilizer is pressed against the heart H. In this manner, a trough-shaped recess W is formed that may fill up with blood and other fluids. The dashed line in FIGS. 7 and 8 shows the path of the surface of the end of the heart in the case in which a stabilizer is not positioned on the surface of the heart H. In particular FIGS. 7B and 8B show that the deepest sites in the trough-shaped recess arise next to the blood vessel. With the stabilizer according to the invention, the aspiration elements 34 are arranged precisely at that location.

A second exemplary embodiment of the present invention is described in detail below with reference to FIG. 7A to 7B.

As can be seen in FIGS. 7A and 7B, the tissue contact component 20 in this exemplary embodiment does not have ski-shaped upward curves. The two bearing elements 21b are formed flat and are connected via a bevel to the base section 22. In such a design, the heart tissue can however be subject to injury at the edges of the bearing elements 21b if the edges of the bearing elements 21b are formed too sharply. In particular at the edge area of the bearing elements 21b, the tissue under the bearing elements 21b is pressed quite strongly which can cause necrosis in the tissue.

A third exemplary embodiment of the present invention is described in detail below with reference to FIG. 8A to 8B.

In this exemplary embodiment, the bearing elements 21c are bent upward in the shape of a ski in all directions in the plane of bearing. In this manner, a tissue contact component 20 is created that particularly protects the heart tissue H. Additional embodiments and variations are obvious to a person skilled in the art from the accompanying drawings and the appended claims. It is for example possible to combine the ski-shaped design of the bearing elements in their longitudinal direction corresponding to FIG. 8A with the flat design thereof in their transverse direction corresponding to FIG. 7B. Of course, the bearing elements can also have different designs. All of the depicted embodiments of the bearing elements in the different directions can be combined as desired.

The invention claimed is:

1. A stabilizer for operations on a heart comprising:
a fastening shaft and
a tissue contact component with two substantially parallel, elongated bearing elements which are provided on a base section and are adapted to be arranged on two opposing sides of a blood vessel (B) such that at least one section of the blood vessel (B) runs between the two bearing elements, wherein the base section of the tissue contact component is affixed to one end of the fastening shaft, wherein
at least one of the bearing elements has a slit that passes through the at least one of the bearing elements from one surface of the at least one of the bearing elements to an opposite surface of the at least one of the bearing elements, and the slit extends in the longitudinal direction of the at least one of the bearing element at least over a section thereof, and
the fastening shaft has an axially proceeding channel which extends at least over a section of the fastening shaft and is connected to at least one connection channel in the region of the end of the fastening shaft to which the base section is affixed, the at least one connection channel configured to connect the axially proceeding channel to an area of the heart.

2. The stabilizer according to claim 1, wherein
the at least one of the bearing elements has at least one groove which extends in a bearing surface of the at least one of the bearing elements substantially perpendicular to its longitudinal direction.

3. The stabilizer according to claim 2, wherein
at least one aspiration component of an aspiration device has at least one radial opening which is connected to the at least one groove in the at least one of the bearing elements when the aspiration device is releasably affixed to the stabilizer, and the at least one aspiration component is partially arranged in the at least one slit in the at least one of the bearing elements.

4. The stabilizer according to claim 1, wherein
a bearing surface of the bearing elements is designed in at least one of the longitudinal direction and the transverse direction of the bearing elements such that the edges of the bearing surface are rounded or curved up like a ski tip.

5. The stabilizer according to claim 1, wherein
a free end of the fastening shaft possesses a connector to which a vacuum device is affixed.

6. The stabilizer according to claim 5, wherein
the connector is a luer connector.

7. The stabilizer according to claim 1, wherein
the fastening shaft has, in the region of the end where the base section is affixed, at least one peripheral groove which is arranged in the vicinity of the at least one connection channel, and is adapted to accommodate a sealing element.

8. The stabilizer according to claim 1, wherein
an axial end of the fastening shaft is closed.

9. A stabilizer for operations on a heart comprising:
a fastening shaft and
a tissue contact component with two substantially parallel, elongated bearing elements which are provided on a base section and are adapted to be arranged on two opposing sides of a blood vessel (B) such that at least one section of the blood vessel (B) runs between the two bearing elements, wherein the base section of the tissue contact component is affixed to one end of the fastening shaft, wherein
at least one of the bearing elements has a slit through the at least one of the bearing elements, and the slit extends in the longitudinal direction of the at least one of the bearing elements at least over a section thereof,
the fastening shaft has an axially proceeding hole which extends at least over a section of the fastening shaft and is connected to at least one connection channel in the region of the end of the fastening shaft to which the base section is affixed, the at least one connection channel configured to connect the axially proceeding channel to an area of the heart,
an aspiration device which is releasably attachable to the fastening shaft, by being pushed onto the fastening shaft from its free end, wherein the aspiration device includes the following:
a connection component with which the aspiration device is fastened releasably on the stabilizer and which has at least one connection cavity that is in fluid communication with the axially proceeding channel when the aspiration device is mounted on the stabilizer, and
at least one aspiration component which has an axially extending channel that is in fluid communication with the at least one connection cavity and which extends at least partially into and along the slit of the at least one of the bearing elements in the longitudinal direction of the at least one bearing element when the aspiration device is mounted on the stabilizer.

10. The stabilizer according to claim 9, wherein
another one of the bearing elements has a longitudinal slit, and
the at least one aspiration component of the aspiration device includes two aspiration components that are connected to the connection component and are adapted to be at least partially arranged in the corresponding slit of the at least one bearing element when the aspiration device is affixed to the stabilizer.

11. The stabilizer according to claim 9, wherein
the aspiration component consists of a curved tube.

12. The stabilizer according to claim 9, wherein
the fastening shaft has, in the region of the end where the base section is affixed, at least one peripheral groove which is arranged in the vicinity of the at least one connection channel, and is adapted to accommodate a sealing element, wherein
the connection component has two peripheral grooves that are formed in an axial passage such that one of these peripheral grooves opposes the at least one peripheral groove in the fastening shaft when the aspiration device is affixed to the stabilizer, wherein the two grooves of the connection component are are adapted to accommodate a sealing component.

13. The stabilizer according to claim 12, wherein
the connection component has an additional peripheral groove between the two other peripheral grooves that at least partially form the at least one connection cavity.

14. The stabilizer according to claim 12, wherein
the sealing component is an O-ring.

* * * * *